US008892208B2

(12) United States Patent
Flynn et al.

(10) Patent No.: US 8,892,208 B2
(45) Date of Patent: Nov. 18, 2014

(54) CLOSED-LOOP NEURAL STIMULATION

(71) Applicant: The Regents of the University of Michigan, Ann Arbor, MI (US)

(72) Inventors: Michael P. Flynn, Ann Arbor, MI (US); Parag G. Patil, Ann Arbor, MI (US); Hyo Gyuem Rhew, Irvin, CA (US); Jaehun Jeong, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 13/917,204

(22) Filed: Jun. 13, 2013

(65) Prior Publication Data

US 2013/0338728 A1 Dec. 19, 2013

Related U.S. Application Data

(60) Provisional application No. 61/659,296, filed on Jun. 13, 2012.

(51) Int. Cl.
| *A61N 1/00* | (2006.01) |
| *A61N 1/36* | (2006.01) |
| *A61N 1/02* | (2006.01) |
| *A61N 1/05* | (2006.01) |
| *A61B 5/04* | (2006.01) |

(52) U.S. Cl.
CPC ............... *A61N 1/36* (2013.01); *A61N 1/0534* (2013.01); *A61B 5/04001* (2013.01); *A61N 1/025* (2013.01); *A61N 1/36067* (2013.01); *A61N 1/36139* (2013.01); *A61N 1/36125* (2013.01)
USPC .......................................................... 607/45

(58) Field of Classification Search
CPC ..................... A61N 1/36139; A61N 1/36135
USPC ........................................................... 607/45
See application file for complete search history.

(56) References Cited

U.S. PATENT DOCUMENTS

| 8,354,881 B2 * | 1/2013 | Denison ............................ 330/9 |
| 8,412,332 B2 | 4/2013 | Massoud-Ansari et al. |
| 2005/0024245 A1 * | 2/2005 | Sit et al. ......................... 341/119 |
| 2005/0213690 A1 * | 9/2005 | Lauer et al. ................... 375/341 |
| 2008/0058893 A1 | 3/2008 | Naujokat et al. |

(Continued)

OTHER PUBLICATIONS

Jongwoo Lee et al., "A 64 ChannelProgrammable [sic] Closed-Loop Deep Brain Stimulator with 8 Channel Neural Amplifier and Logarithmic ADC," *Symposium on VLSI Circuits Digest of Technical Papers*, 76-77 (Jun. 2008).

(Continued)

*Primary Examiner* — Robert N Wieland
(74) *Attorney, Agent, or Firm* — Marshall, Gerstein & Borun LLP

(57) ABSTRACT

A system and method for conducting closed loop deep brain stimulation on an individual, and more specifically, for receiving local field potential neural signals, encoding and filtering the signals into the logarithmic domain, processing the signals, and determining optimal stimulation parameters for deep brain stimulation based on the processed neural signals. The system and method may also include an RF-DC converter such that the system may be powered in whole or in part based on radio frequency signals. The system and method may also include an RF transceiver such that the system may transmit data wirelessly to an external receiver, or may receive stimulation parameters wirelessly from an external transceiver.

19 Claims, 21 Drawing Sheets

(56) References Cited

U.S. PATENT DOCUMENTS

2008/0243022 A1* 10/2008 Donnett et al. ............... 600/544
2008/0309536 A1* 12/2008 Le Guillou et al. ........... 341/143
2011/0193633 A1* 8/2011 Yoon et al. .................... 330/260
2012/0059438 A1* 3/2012 De Ridder ...................... 607/70

OTHER PUBLICATIONS

Jongwoo Lee et al., "A 64 Channel Programmable Closed-Loop Neurostimulator with 8 Channel Neural Amplifier and Logarithmic ADC," *IEEE Journal of Solid-State Circuits*, 45(9):1935-45 (Sep. 2010).

Giuseppe Papotto et al., "A 90-nm CMOS Threshold-Compensated RF Energy Harvester," *IEEE Journal of Solid-State Circuits*, 46(9):1985-97 (Sep. 2011).

Hyo-Gyuem Rhew et al., "A Wirelessly Powered Log Based Closed-Loop Deep Brain Stimulation SoC with Two-Way Wireless Telemetry for Treatment of Neurological Disorders," presented at *Symposium on VLSI Circuits* (*VLSIC*), Honolulu, HI, 2 pages (Jun. 14, 2012).

* cited by examiner

CLOSED-LOOP NEURAL STIMULATION

CROSS REFERENCE TO RELATED APPLICATIONS

The present application claims the benefit of priority to U.S. Provisional Application No. 61/659,296, filed on Jun. 13, 2012, which is hereby incorporated by reference herein in its entirety.

FIELD OF TECHNOLOGY

The following disclosure relates to systems and methods for conducting closed-loop neural stimulation and, in particular, for conducting closed-loop neural stimulation in treatment of various neurological disorders.

BACKGROUND

More than 10 million people in the U.S. suffer from movement disorders such as essential tremor, dystonia, and Parkinson's disease. Additionally, over three million people in the U.S. and over 50 million people worldwide suffer from epilepsy. One of the most effective emerging treatments for these diseases is deep brain stimulation (DBS) of the subthalamic nucleus with periodic, high frequency electric pulse trains. DBS has been federally approved for treatment of various movement disorders, with the FDA approving DBS treatment of essential tremor in 1997, Parkinson's disease in 2002, and dystonia in 2003.

Treatment of a patient using DBS requires adapting high frequency electrical pulse trains to match individualized patient needs. Such customized treatment is achieved through adjustment of stimulation parameters such as amplitude, pulse width, and repetition rate (frequency). Though research on DBS has been ongoing for over a decade, the underlying principles of DBS are still not clear. Consequently, the parameters for DBS treatment have traditionally been set based on an analysis of visual signs of symptoms.

Using visual symptoms to analyze and set electrical stimulation parameters requires that the patient, after receiving a surgical DBS implant, return to a neurologist or trained technician such that the neurologist or technician may monitor symptoms and alter parameters accordingly using an external component to wirelessly transmit instructions to the implanted neurostimulator. This process takes 3-5 hours, and must be undertaken by the patient frequently in the first 3-6 month period, and periodically after that as symptoms change. This type of system currently in place is called open-loop DBS.

The DBS process may be substantially simplified by using a dedicated microprocessor to determine the proper stimulation parameters automatically, thus obviating the need for a neurologist or technician to repeatedly conduct this task manually based on assessment of visual symptoms. This simplified process is known as closed-loop DBS.

Though the precise principles of DBS are not yet known, it is commonly understood that calibration of stimulation parameters may be reasonably obtained through measurement of one or both of two neural signals: spike signals, also known as action potentials, and local field potential (LFP) signals. One existing approach to DBS utilizes the first of these signals, spike signals, in conjunction with principal component analysis (PCA). Although this method can disentangle spike signals from each other and from background noise, it is extremely computation-intensive, making long term power supply of this type of DBS device by radio frequency or battery infeasible. Further, recent studies have shown that the latter signal, LFP, is in fact a more effective DBS feedback indicator. Current closed-loop DBS approaches are therefore too power intensive to be feasible as a long-term RF or battery-powered solution, and they fail to utilize the more effective LFP signals, instead focusing primarily on spike signals.

SUMMARY

Disclosed herein is a system and method for conducting closed-loop neural stimulation. This electrical stimulation can provide treatment for various neurological disorders. While the precise mechanism of DBS is not fully known, disclosed herein is a system and method that take advantage of recent findings, making closed-loop neural stimulation possible for the first time. Namely, the system and method utilize measurements of local field potential energy in the brain to customize electrical stimulation waves to be administered into the brain for treatment of neurological disorders.

In some embodiments, the method may include receiving neural signals from the brain. These neural signals may consist of either or both of two signals: local field potential (LFP) signals and high frequency spike signals. The method also may include recording the signals into a memory, amplifying the received signals via an amplifier module, and encoding the amplified signals in the digital logarithmic domain via a logarithmic analog-to-digital converter module. The method further may include filtering in the log domain, via a logarithmic digital filter module, the received neural signals. The method may also include measuring the filtered signals and calculating at least one optimal stimulation parameter via a programmable digital PI-controller within a digital signal processor. The method also may include generating, via a stimulator module, a stimulation based on calculated optimized stimulation parameters. The method may further include transmitting the generated stimulation signal to an individual.

In other embodiments, an apparatus may include an amplifier used to receive, record, and/or amplify neural signals received from a brain. The apparatus may include a logarithmic analog-to-digital converter module to encode the received neural signals into the digital domain. The apparatus may also include a logarithmic digital filter module to filter the received neural signals, and a digital signal processor module to measure the received neural signals. The apparatus may further include a digital PI-controller within the digital signal processor to determine optimal stimulation parameters based on neural signal measurements.

In some embodiments, the system or method may further comprise a power management module, including a radio frequency-DC converter module, capable of providing power to at least one of the amplifier module, logarithmic analog-to-digital converter module, logarithmic digital filter module, digital signal processor, and stimulator module. This allows use of a DBS device without the inherent complications of battery installation within a human body, including the risk of wire erosion, wire snapping, battery corrosion, and periodic surgeries for battery replacement. In these embodiments, the power management block may be composed of a RF-DC converter, low-dropout regulators (LDOs), and bandgap reference circuits, supplying 1.8V from a 915 MHz carrier to the entire DBS system.

In some embodiments, the system or method may further comprise a clock generator module. A relaxation oscillator may be used in these implementations in place of an LC based oscillator, which is impractical due to its large size of inductor needed to achieve a slow clock speed. One possible relaxation oscillator is a source-coupled multivibrator, desirable for its simple structure and small number of circuit components. This multivibrator can be implemented to generate a 800 kHz on chip clock signal for the entire system.

In some embodiments, the system or method may further comprise a radio frequency transceiver for monitoring the state of the patient or the device itself, among other tasks. A low-power backscatter based RF transceiver may be used for its extremely low power consumption and simplicity of design on the transponder side. A 800 kbps power-efficient backscatter RF transmitter may communicate recorded LFP, spike, or raw data wirelessly to an external receiver for further analysis. Alternatively, the RF transceiver may also receive stimulation parameters manually set by a doctor or technician and transmitted wirelessly.

DETAILED DESCRIPTION

The disclosed system and method may utilize a closed-loop DBS system to provide treatment of various neurological disorders, including essential tremor, dystonia, and Parkinson's disease. This treatment may involve stimulation of the subthalamic nucleus with periodic, high frequency electric pulse trains. Because each individual's brain responds differently to such signals, stimulation parameters should be set individually for each patient to provide optimal treatment. Stimulation signals may be adjusted by varying parameters such as amplitude, pulse width, and repetition rate.

Instead of a neurologist or technician determining stimulation parameters through visual observation of symptoms, the method herein disclosed can determine and set these parameters automatically based on measurements of signals in the brain. Though the underlying principles of DBS are not yet known, it is understood that two particular brain signals, local field potential (LFP) signals and spike signals, provide feedback information useful in setting stimulation parameters. Spike signals, also known as action potentials, can have bandwidths from 100 Hz to 10 kHz and amplitudes up to 500 $\mu V$. LFP signals can have bandwidths from 1 Hz to 100 Hz and amplitudes up to 5 mV. Neural spike signals were traditionally thought to be the best feedback indicators for DBS treatment. However, recent research suggests that LFP signals are in fact much better DBS feedback indicators.

Figure 1:
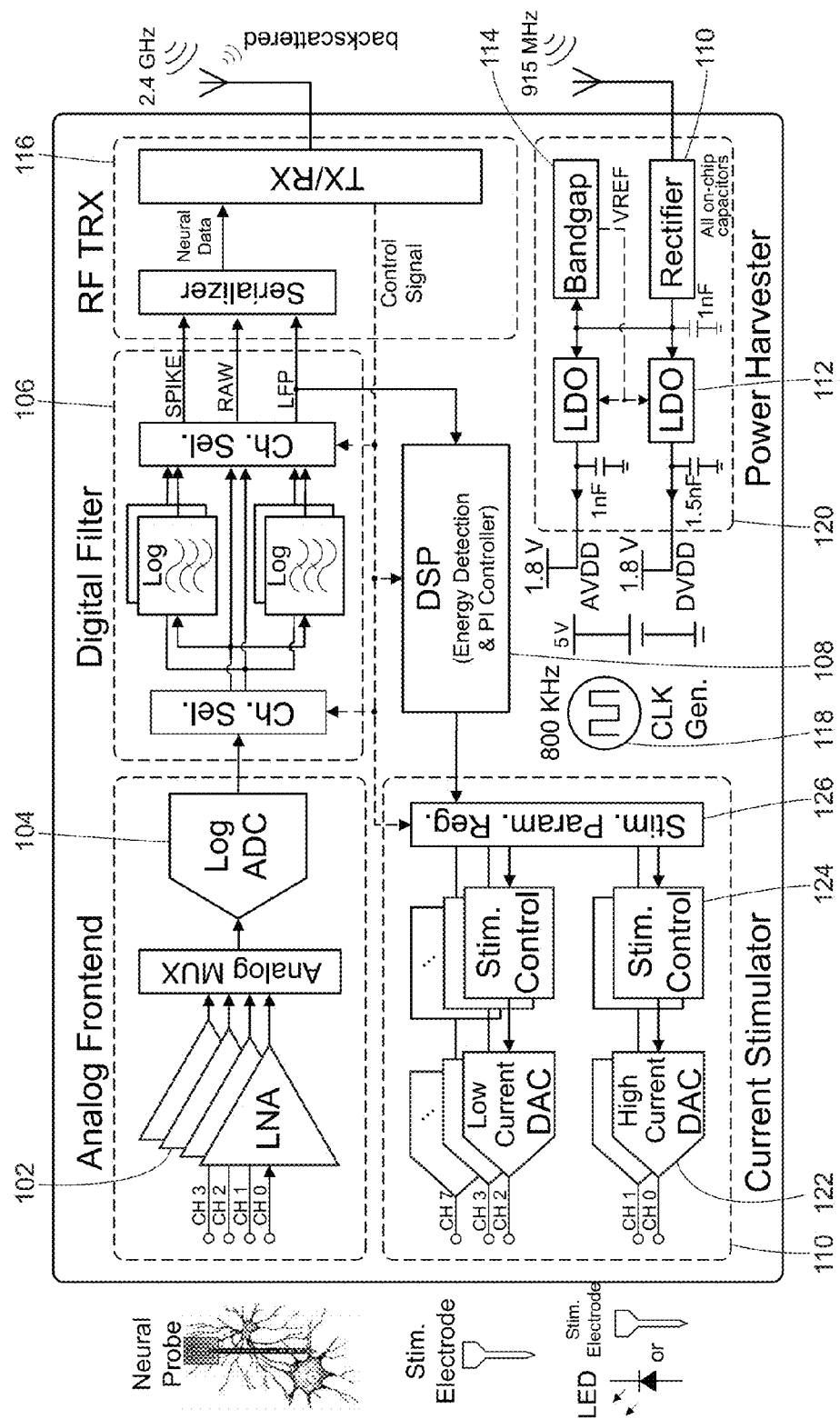
FIG. 1 is a diagram of one embodiment of a log-based closed-loop deep brain stimulating device.

FIG. 1 provides an overview of one embodiment of closed-loop DBS. First, neural signals may be received from a brain. In one embodiment these signals may be comprised of local field potential signals (LFP) and/or high frequency spike neural signals. These signals may be received and amplified by low-noise neural amplifier modules 102. A logarithmic analog-to-digital converter module (ADC) 104 may then encode the neural signals into the digital domain. A logarithmic digital filter module 106 may then filter the received signals, at which point a digital signal processor 108 may determine the optimal stimulation parameters based on the neural signal measurements. A stimulator module 110 may then generate stimulation based on the calculated optimized stimulation parameters. In one embodiment, a power harvester 120 may be used to convert radio frequency waves to DC energy. The power harvester is composed of low-dropout regulators (LDOs) 112, a rectifier 110, and a bandgap reference 114. In one embodiment, a clock generator 118 may be implemented to generate a clock signal. A detailed description of the DBS process follows.

Figure 2:
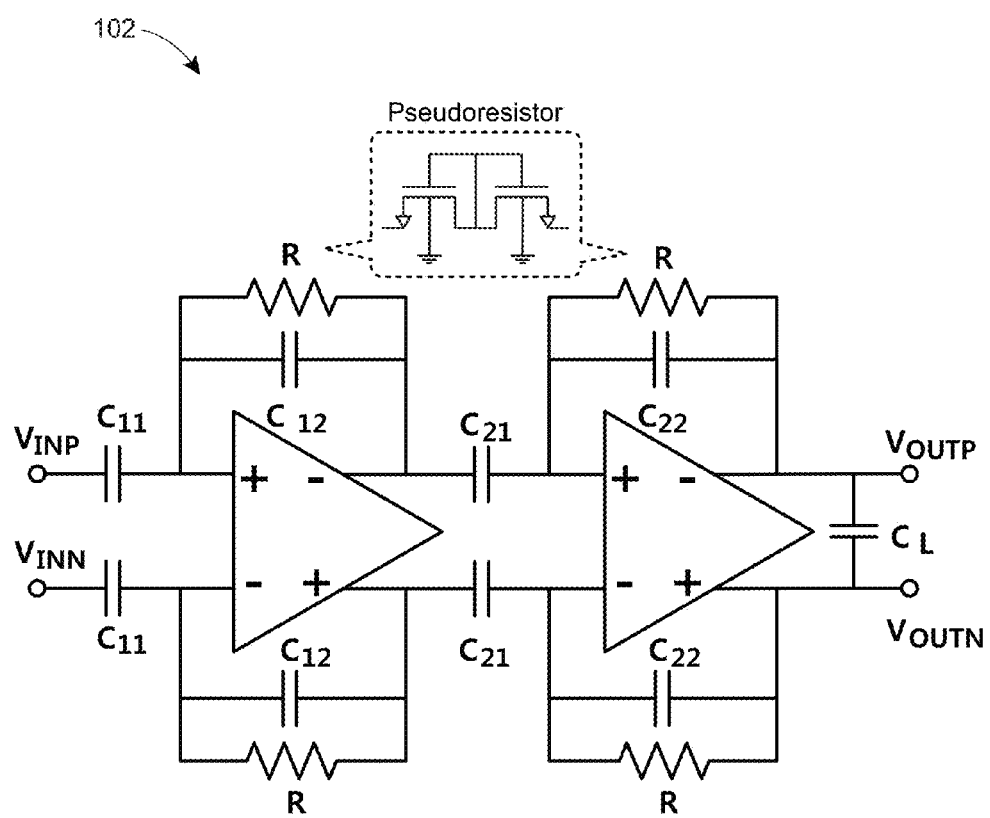
FIG. 2 is a schematic of one embodiment of a band-pass amplifier with a two-stage cascade structure.

The disclosed system and method may first utilize low-noise neural amplifiers (LNAs) 102 to receive, record and amplify both LFP and spike signals from the brain. Because these signals exhibit different bandwidth and amplitude characteristics, there are few integrated circuit (IC) systems capable of recording both simultaneously. In order to achieve this, the LNAs 102 should exhibit a high dynamic range, good noise performance, and wide bandwidth. Rather than use a traditional general band-pass amplifier, the disclosed system and method may implement a two-stage cascade structure to achieve these characteristics, as shown in FIG. 2. Such a configuration allows for an appropriately high gain while suppressing out-of-band signals and reducing noise.

Still referring to FIG. 2, the first stage may have a pass-band gain higher, e.g. 50, than the pass-band gain of the second stage, e.g. 10. The larger gain in the first stage may reduce the effect from the second stage to the input-referred noise of the entire LNA while keeping the total capacitor area manageable. The amplifiers in the first and second stages may be folded cascode amplifiers with an NMOS input pair to provide sufficient gain. The input pair of amplifiers may be sized to W=20 μm and L=20 μm to reduce total noise. A pseudoresistor comprised of two back-to-back diode-connected NMOSs may be used to emulate high resistance.

Once neural signals are recorded and amplified by LNAs 102, the signals may be encoded into the digital domain using a pipeline logarithmic analog-to-digital converter (ADC) 104 to facilitate digital processing. Using a logarithmic ADC rather than a linear ADC presents several advantages. Neural signals, like many other real-world signals, are best represented on a logarithmic rather than linear scale. These signals exhibit a high dynamic range and require high-resolution analog to digital conversion under a conventional linear encoding scheme. However, this increased ADC resolution results in larger area consumption, higher power consumption, or slower conversion speed. Alternatively, a variable gain amplifier (VGA) can be used to expand dynamic range, but VGA is generally slow and responds poorly to fast varying signals. Use of a pipeline logarithmic ADC, by contrast, presents none of these issues.

The transfer function of pipeline logarithmic ADC is as follows:

$$\left[2^N \cdot \log_B\left(B \cdot \frac{V_{in}}{V_{range}}\right)\right] = b_{N-1} 2^{N-1} + \ldots + b_0$$

The transfer function assumes an N-bit logarithmic ADC with an input voltage, $V_{in}$, a full-scale input range, $V_{range}$, output digital bits $b_{N-1}$-$b_0$, and the base of logarithm function, B.

The least significant bit size increases as the input signal level increases, as dictated by the following:

$$LSB_j = V_{range} \cdot B^{\left(\frac{j}{2^N}-1\right)} \cdot \left(B^{\frac{1}{2^N}} - 1\right), \text{ where } j = 0, 1, 2, \ldots, 2^N - 1$$

The maximum and minimum bit size, therefore, are given by:

$$LSB_{max} = V_{range} \cdot \left(1 - B^{-\frac{1}{2^N}}\right),$$

$$LSB_{min} = V_{range} \cdot \left(B^{\left(\frac{1}{2^N}-1\right)} - B^{-1}\right).$$

The dynamic range (DR) is defined as the ratio of the input range to the smallest resolvable signal, as described by:

$$DR = \frac{V_{range}}{LSB_{min}} = \frac{B}{B^{\frac{1}{2^N}-1}}$$

Therefore, as the base of the logarithmic function, B, and the resolution, N, increase, DR also increases. Because of this logarithmic scale coding, a log-ADC has a higher DR than a conventional linear ADC.

Figure 3:
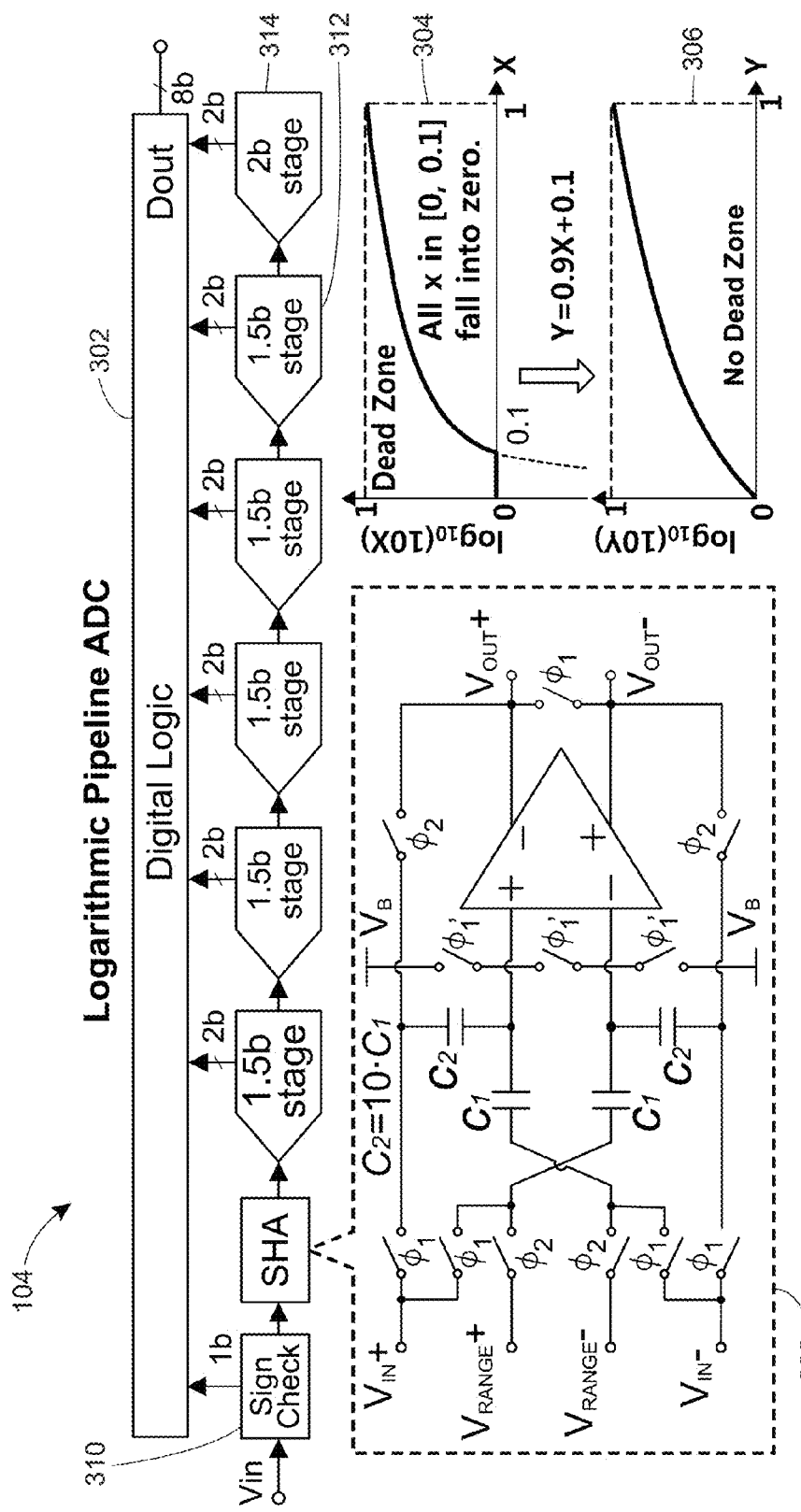
FIG. 3 is a diagram of one embodiment of an 8-bit pipeline logarithmic analog-to-digital converter (ADC) with a graph showing the effect of pre-conversion of ADC input to avoid logarithmic dead zone.

As shown in FIG. 3, all logarithmic ADC inputs smaller than $0.1 \times V_{range}$ are converted to a digital output 0 losing the benefit of high DR characteristic of logarithmic conversion. This logarithmic dead zone can be overcome with a pre-conversion of the input signal. With B=10, for example, input x is pre-converted to y=0.9x+0.1, where y is the input to logarithmic conversion. This pre-conversion scheme effectively eliminates the log dead-zone without losing significant DR. A pre-conversion graph is shown at 304, and a post-conversion graph is shown at 306.

Before pre-conversion the polarity of the input signal 310 may be checked and, if necessary, converted to a positive number as required by the logarithmic function. After the sign decision and pre-conversion, five 1.5-bit stages 312 and a 2-bit flash ADC 314 may process the signal and a digital logic block 302 may calculate the 8-bit digital output.

Direct logarithmic conversion of a 1.5-bit stage in linear domain requires a squaring operation to replace multiplication-by-2 in the linear domain and conditional multiplication to replace the conditional addition or subtraction in the linear domain. This circuitry is shown at 308. To avoid analog squaring, the reference voltages for the comparators and the gain settings for conditional addition are scaled in order to achieve the same result. The reference voltages for a $j^{th}$ 1.5-bit stage are given by:

$$V_{ref0j} = V_{range} \cdot B^{-1.25/2^j}$$

$$V_{ref1j} = V_{range} \cdot B^{-0.75/2^j},$$

where $V_{ref0j}$ and $V_{ref1j}$ are the first and second reference voltages for a $j^{th}$ 1.5-bit stage, and $V_{range}$ is the full scale input range. The gain settings for a $j^{th}$ 1.5-bit stage are given by:

$$G_j(V_{in}) = \begin{cases} G_{0j} = B^{1/2^j}, & V_{in} \leq V_{ref0j} \\ G_{1j} = B^{1/2^{j+1}}, & V_{ref0j} < V_{in} \leq V_{ref1j} \\ G_{2j} = 1, & V_{ref1j} < V_{in} \leq V_{range} \end{cases}$$

where $G_{0j}$, $G_{1j}$, and $G_{2j}$ are gains for the first, second, and third input region for a $j^{th}$ 1.5-bit stage, respectively, and $V_{range}$ is the full scale input range.

Returning to FIG. 3, one embodiment of an 8-bit logarithmic ADC with one sign bit and a base of 10 is shown. A sampling rate of 100 kSample/s may be chosen to process neural data from four recording channels simultaneously with some bandwidth margin. This configuration (7-bit resolution+1 sign bit) provides a DR of 61 dB, which is high enough to cover the entire range of spike and LFP signals.

Figure 4:
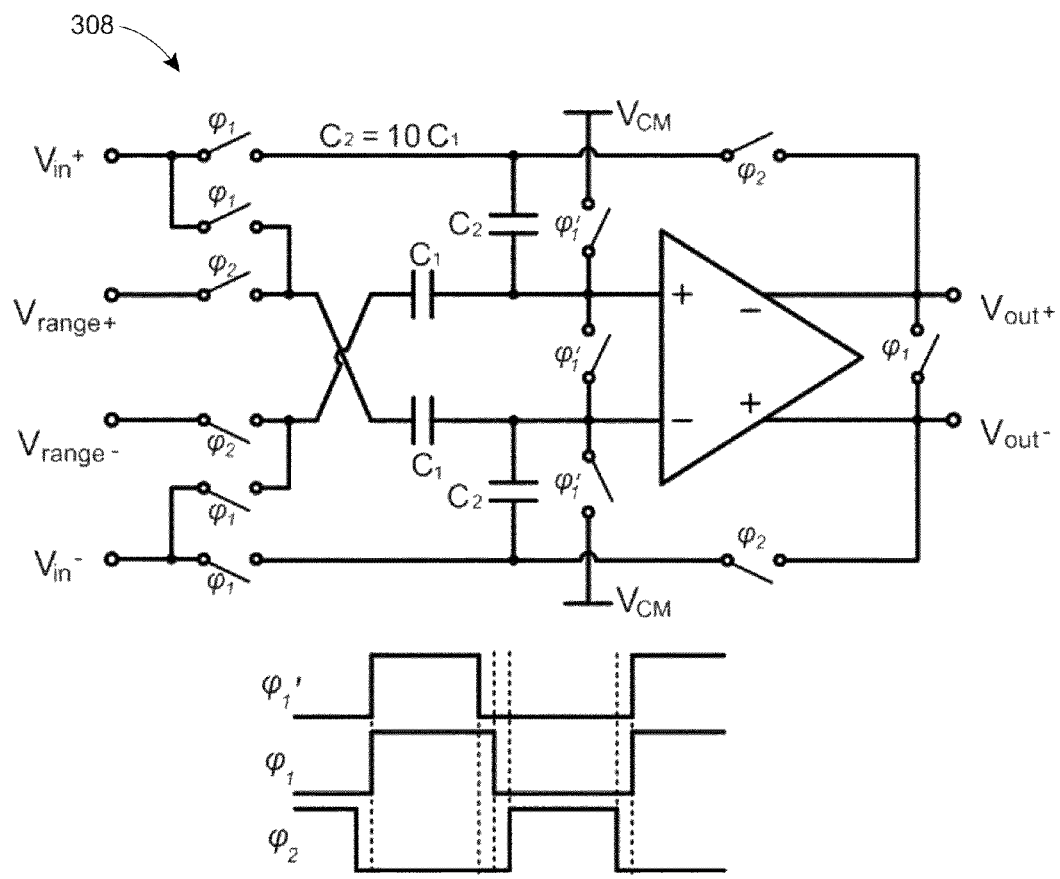
FIG. 4 is a diagram depicting one embodiment of a fully differential sample and hold (SHA) circuit that embeds the pre-conversion scheme.

FIG. 4 illustrates an example of a fully differential sample and hold circuit 308 that embeds the pre-conversion scheme. A common mode voltage of 800 mV may be used throughout the entire ADC 104. Three clock signals $\phi_1$, $\phi_1'$, and $\phi_2$ may control the operation of the sample and hold circuits with the help of bottom-plate sampling. When $\phi_1$ is high, the stage input may be sampled and the output may be reset. When $\phi_2$ is high, the input is amplified and the output is set by the following equation:

$$V_{out} = 0.9 \cdot V_{in} + 0.1 \cdot V_{range}$$

For the op-amps in the SHA block 308 and the 1.5-bit stages 312 shown in FIG. 3, a folded cascade amplifier with a PMOS input pair 308 may be used for its high gain and low power consumption. The full scale input range, Vrange, may be set to 600 mV which is the maximum achievable voltage swing that allows all MOS devices in the cascode amplifiers in saturation region. The amplifiers are scaled through the stages to match the gain-bandwidth requirement.

Figure 5:
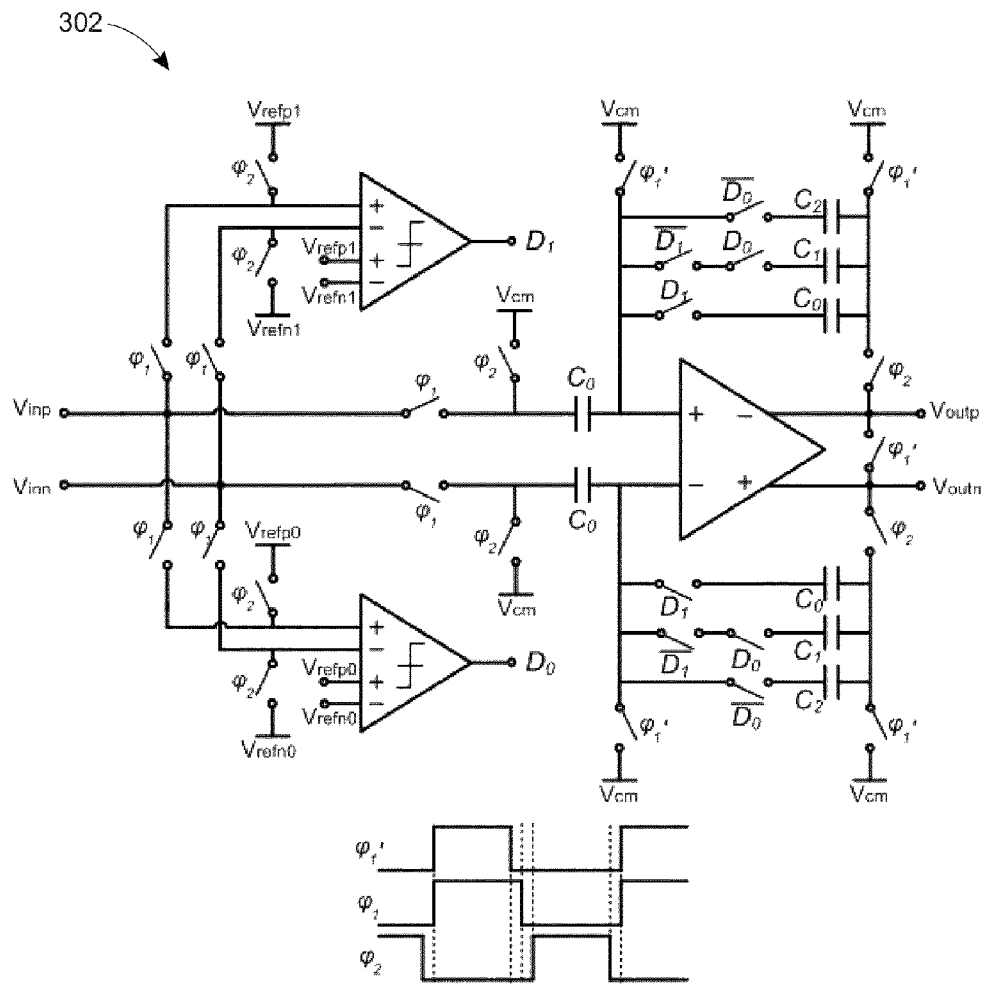
FIG. 5 is a diagram depicting one embodiment of a simplified schematic of a logarithmic 1.50 bit stage of the logarithmic ADC.

FIG. 5 shows a schematic of a fully differential 1.5-bit stage 312 of the logarithmic ADC 104. As in the SHA block 308 shown in FIG. 3, three clock signals, $\phi_1$, $\phi_1'$, and $\phi_2$, control the operation of the sample and hold circuits with the help of bottom-plate sampling. When $\phi_1$ is high, the stage input may be sampled and the output may be reset. When $\phi_2$ is high, comparators decide the output bits and the residue is amplified with a gain depending on the bit decision. A two-stage regenerative comparator is used for the sign decision block 310 and 1.50-bit stages 312, and the size of the input pairs of the comparators are scaled through the stages as the mismatch requirement becomes more strict due to the decrease of input range along the stages.

Figure 6:
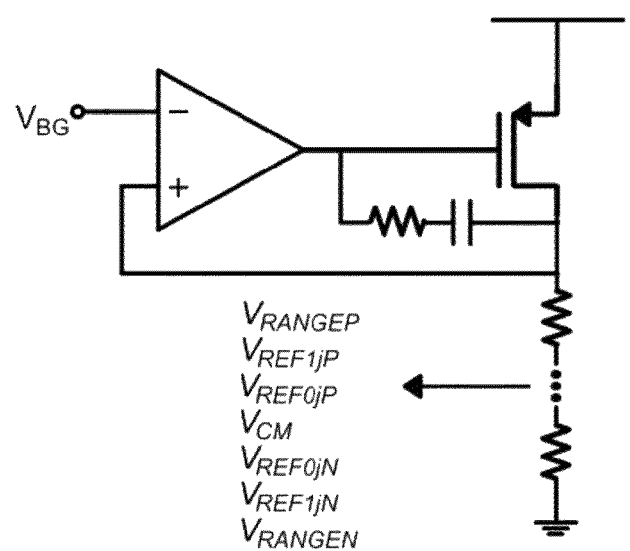
FIG. 6 is a schematic of one embodiment of a bias circuit.

FIG. 6 shows a schematic of a bias circuit, which is used to generate reference voltages of the ADC 104. The bias circuit is implemented entirely on-chip to enable the single-chip operation of the neural stimulation SoC. The schematic of the bias circuits is comprised of a two-stage amplifier with frequency compensation and a resistor ladder. The common mode voltage and differential full scale input range voltages, as well as the differential reference voltages, are generated from the bias circuits.

Figure 7:
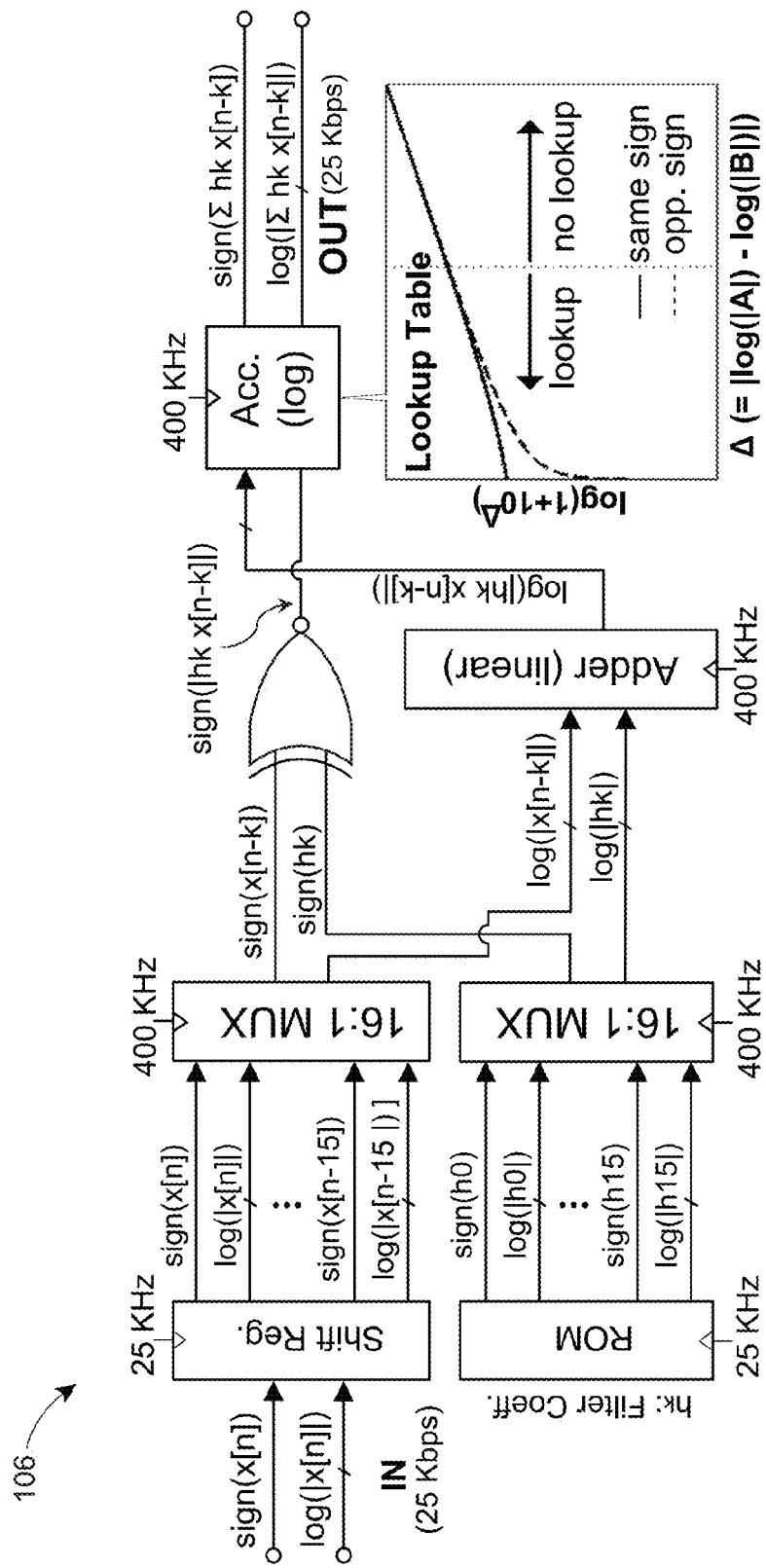
FIG. 7 is a schematic of one embodiment of a logarithmic digital FIR filter.

Once neural signals are expressed digitally in logarithmic scale after passing through a pipeline logarithmic ADC 104, the signals may be passed through log domain digital filters 106 to separate the low frequency LDF signals from the high frequency spike signals, as shown in FIG. 7. Using logarithmic arithmetic, the LFP energy may be calculated from the filtered LFP signals and later used by the programmable closed-loop digital PI-controller within a digital signal processor 108 to set the optimal stimulation parameters.

Filtering in the logarithmic domain presents several advantages over filtering in the linear domain. For a given DR requirement, for example, fewer bits are needed for a logarithmic number system compared to the conventional linear number system. Furthermore, multiplication in linear-domain is equivalent to addition in logarithmic domain as described by:

$$\log(X \cdot Y) = \log X + \log Y$$

where X and Y are positive numbers. This equation suggests that power-consuming multipliers may be substituted with adders, which, in conjunction with fewer required bits, leads to lower power consumption for a digital processing unit.

Linear-domain addition is less intuitive in the log-domain, but several existing methods simplify this process. One method is to use a lookup table, a particularly simple solution.

$$\log(X+Y) = \log\left(X\left(1+\frac{Y}{X}\right)\right) = \log X + \log(1+10^{\log Y - \log X})$$

In the above equation, as the value of log Y–log X becomes larger, $1+10^{\log Y - \log X}$ approximates $10^{\log Y - \log X}$, which is easily calculable. In the case that log Y–log X is not large enough, a lookup table is needed to find the value of $\log(1+10^{\log Y - \log X})$. There exists a threshold value beyond which $10^{\log Y - \log X}$ and $1+10^{\log Y - \log X}$ are the same, as seen in FIG. 7. Therefore, a lookup table is needed only when log Y–log X is smaller than that threshold.

As shown in FIG. 7, a 15$^{th}$ order digital FIR low-pass filter (LPF) and a high-pass filter (HPF) may be implemented in the system to separate the low frequency LFPs and the high frequency neural spikes from the digitized neural data and to provide those signals simultaneously. The digital filters may be run with a 400 kHz clock. Both the LPF and the HPF may each have the same 3 dB cutoff frequency of 700 Hz.

Figure 8:
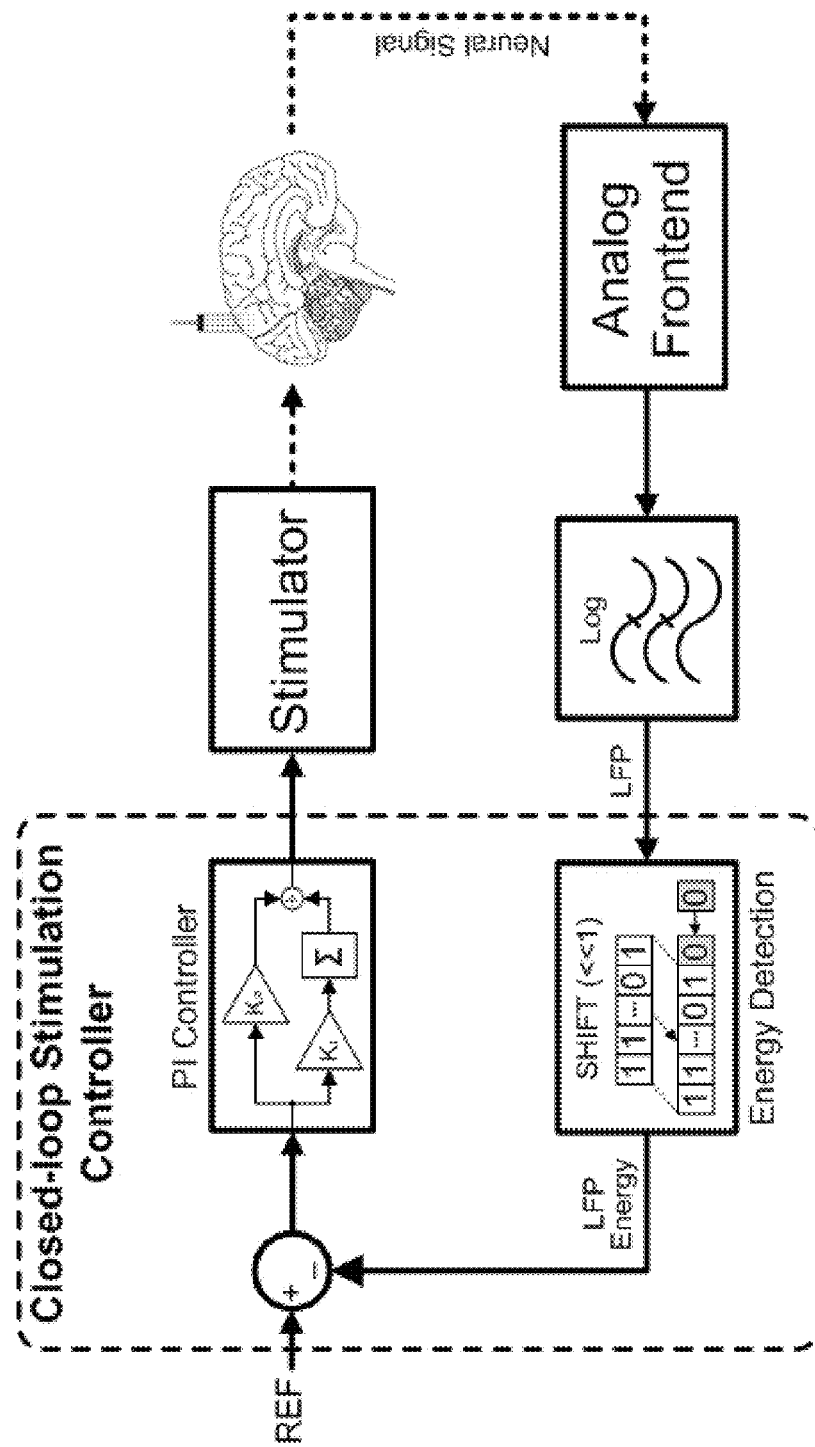
FIG. 8 is a flow diagram of one embodiment of a closed-loop stimulation showing the interior functionality of the stimulation controller.

After the LPF and spike signals are separated using digital filters, the filtered LFP signal may be measured and used to determine stimulation parameters by a PI controller within a digital signal processor 108, as shown in FIG. 8. The energy of the log-domain LFP signal may be calculated by a digital signal processor 108 using simple logical 1-bit left-shifting. To generate the appropriate output parameters, the product of the controller constants and the controller input may be calculated in the log domain through simple addition.

In one embodiment, the system and method may use a power management block 120 to power the system, obviating the need for a battery or AC power source. The power management block 120 may be made up of a RF-DC converter 110, low-dropout regulators (LDOs) 112, and bandgap reference circuits 114.

Figure 9:
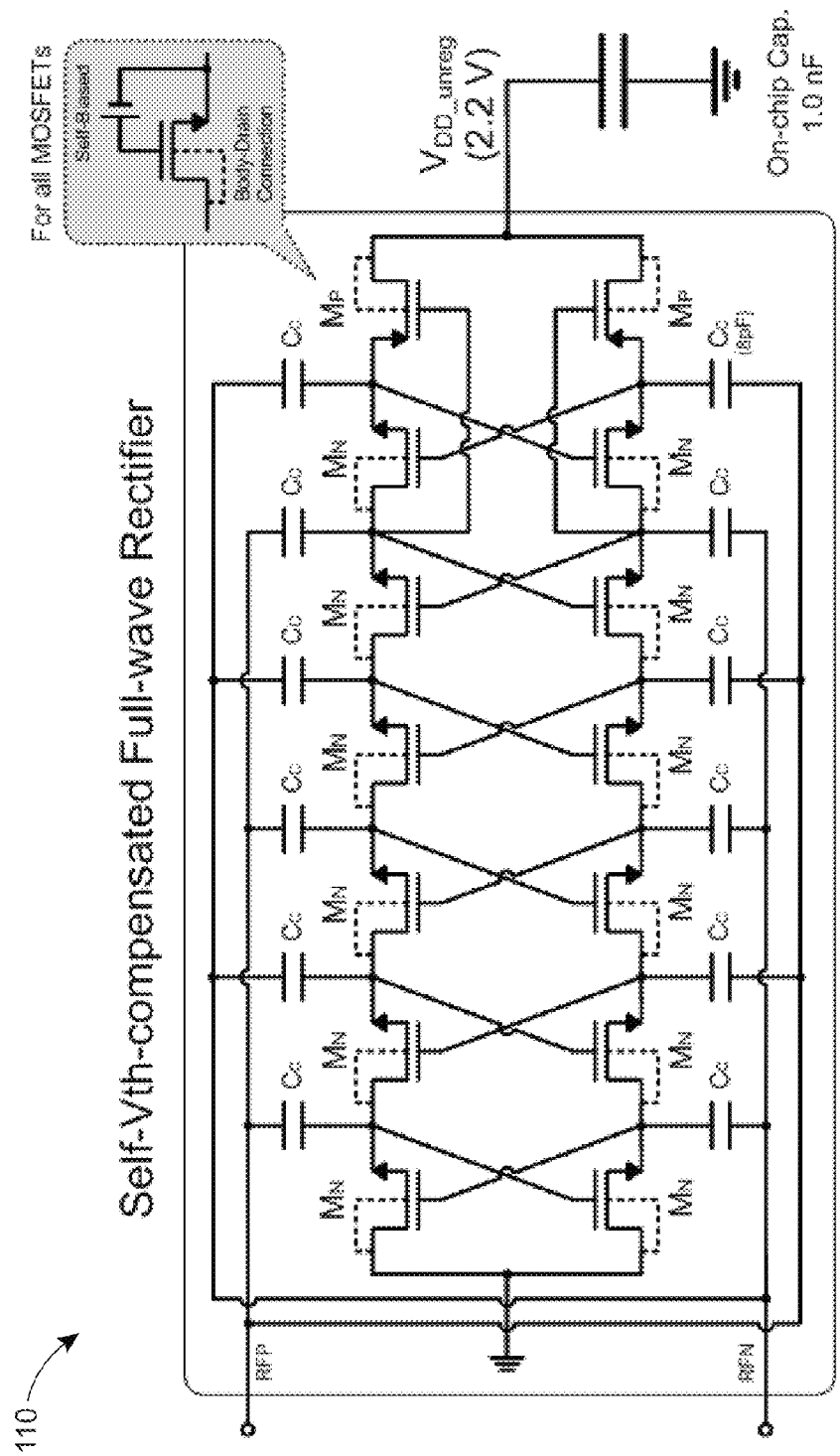
FIG. 9 is a schematic of one embodiment of a full-wave rectifier that generates unregulated Vdd of 2.2 V from 915 MHz carrier.
Figure 19:
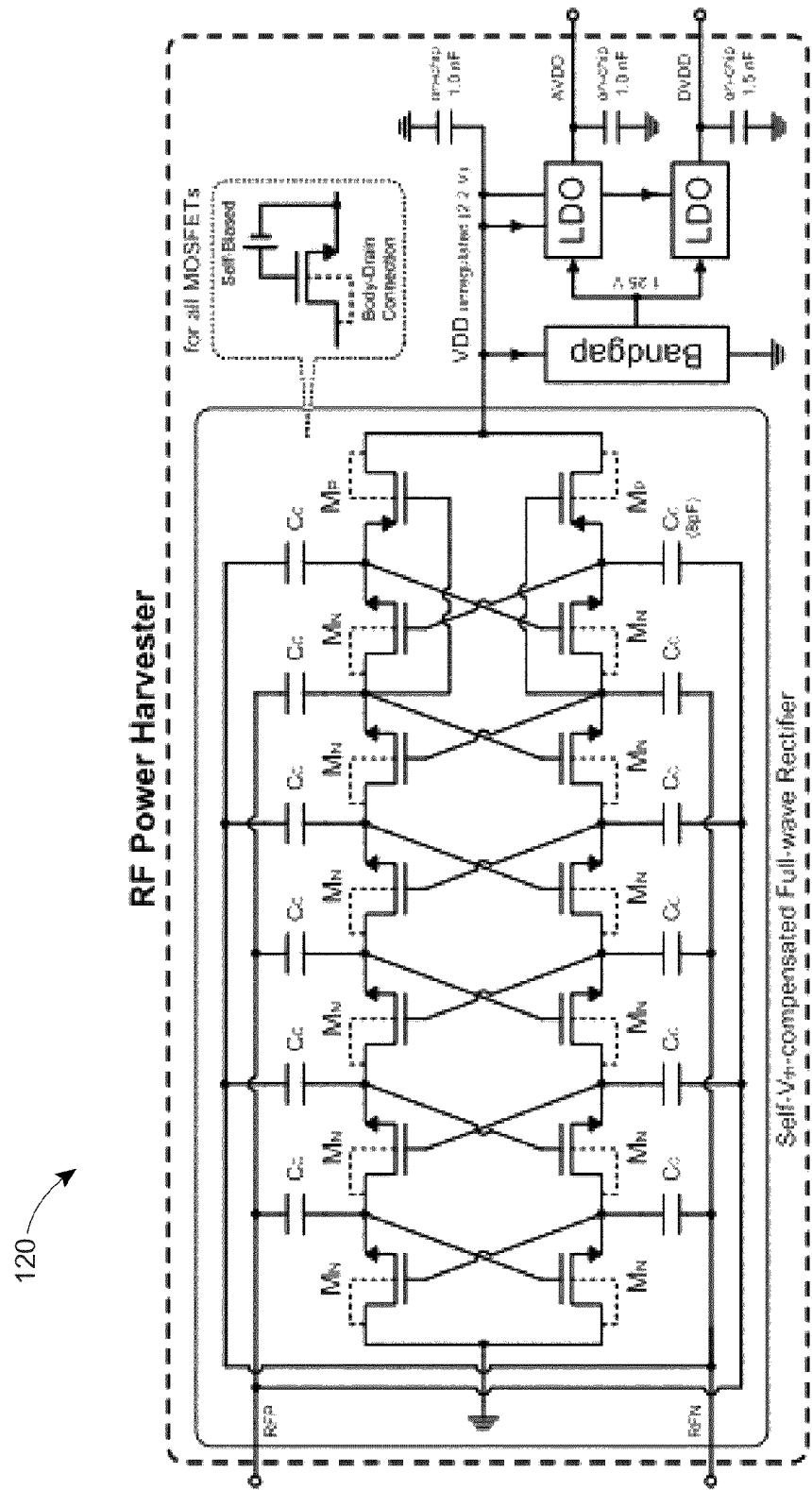
FIG. 19 is a block diagram of one embodiment of a power management block.

As shown in FIG. 9, the RF-DC converter 110 may make up one element of the power management block. Input of the RF-DC converter may be connected to an antenna that receives a 915 MHz carrier. A full-wave self-threshold-compensated rectifier may be used, which can generate unregulated $V_{DD}$ of 2.2V and charges $V_{DD}$ on a 1 nF on-chip capacitor, as shown in FIG. 19. Additionally, as shown in FIG. 9, the body of each FET may be tied to the drain for reduced on-resistance and reverse-biased leakage.

Figure 10:
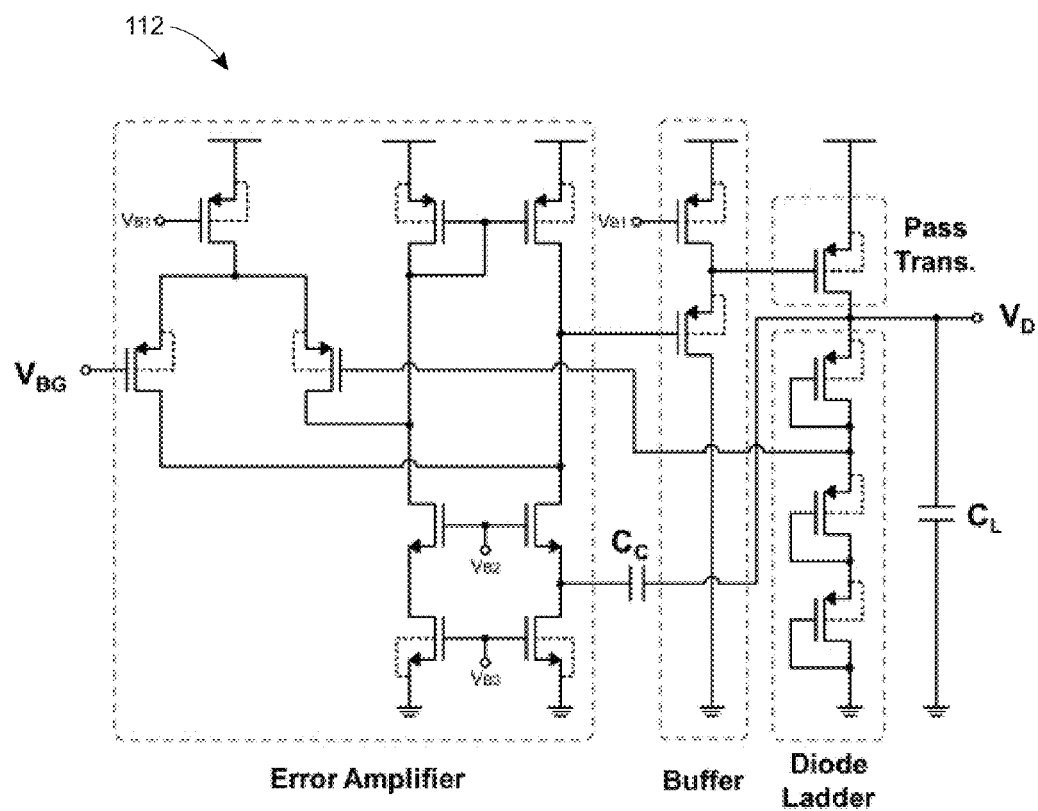
FIG. 10 is a schematic of one embodiment of a low-dropout regulator (LDO).

A low-drop regulator (LDO) 112 may make up another element of the power management block, as shown in FIG. 10. The output voltage, $V_{DD}$, may be set by the diode ladder and bandgap reference voltage, $V_{BG}$. The LDOs 112 may be designed to be fully on-chip requiring no external on-board passive components to achieve small size and single-chip operation capability of the proposed closed-loop stimulation system. The frequency compensation capacitor, $C_C$, may be used to provide a high frequency path.

Figure 11:
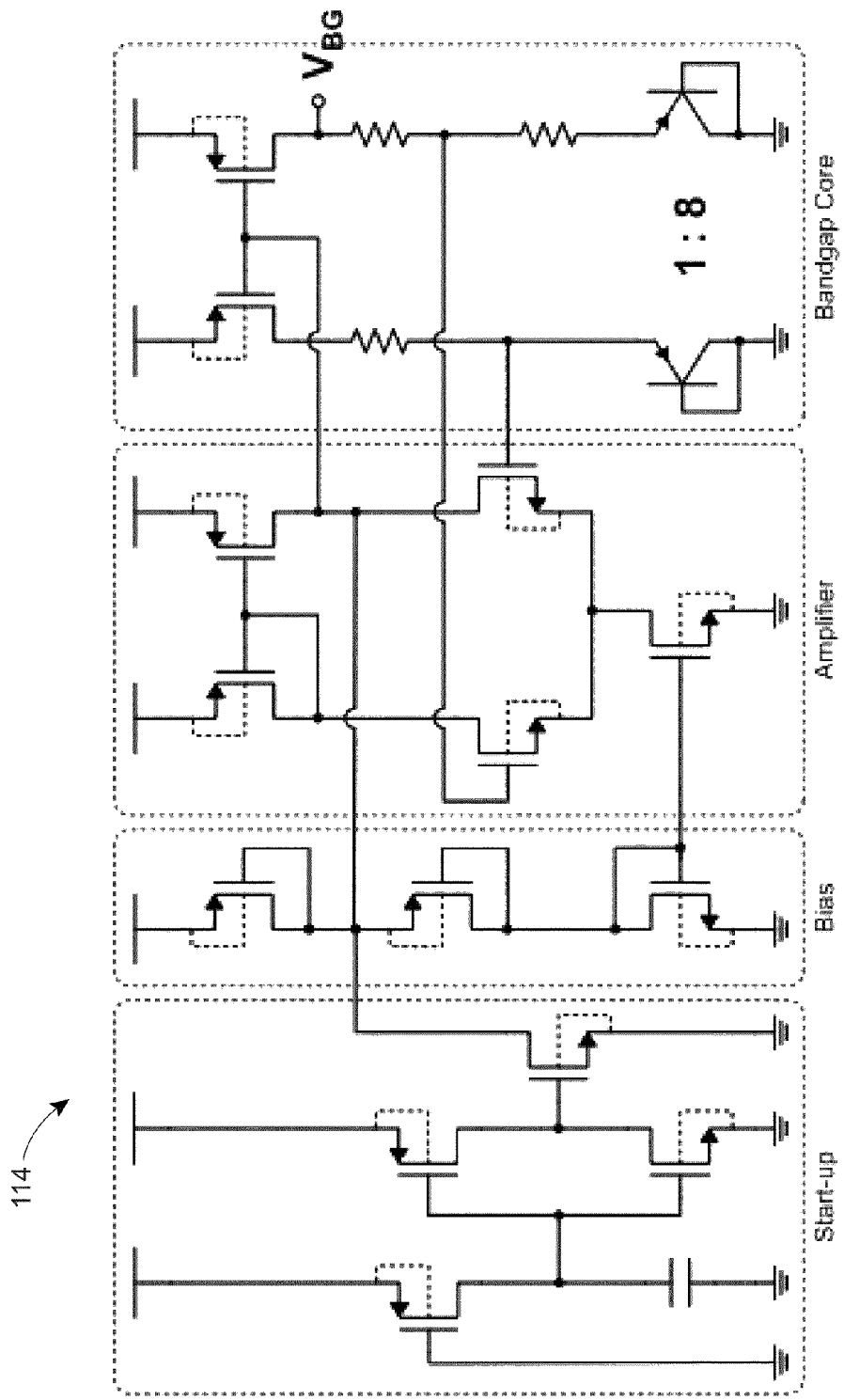
FIG. 11 is a schematic of one embodiment of a bandgap reference circuit.

As shown in FIG. 11, the bandgap voltage reference 114 may make up another element of the power management block. The bandgap reference 114 may be used to provide a stable voltage reference throughout the entire system.

Figure 12:
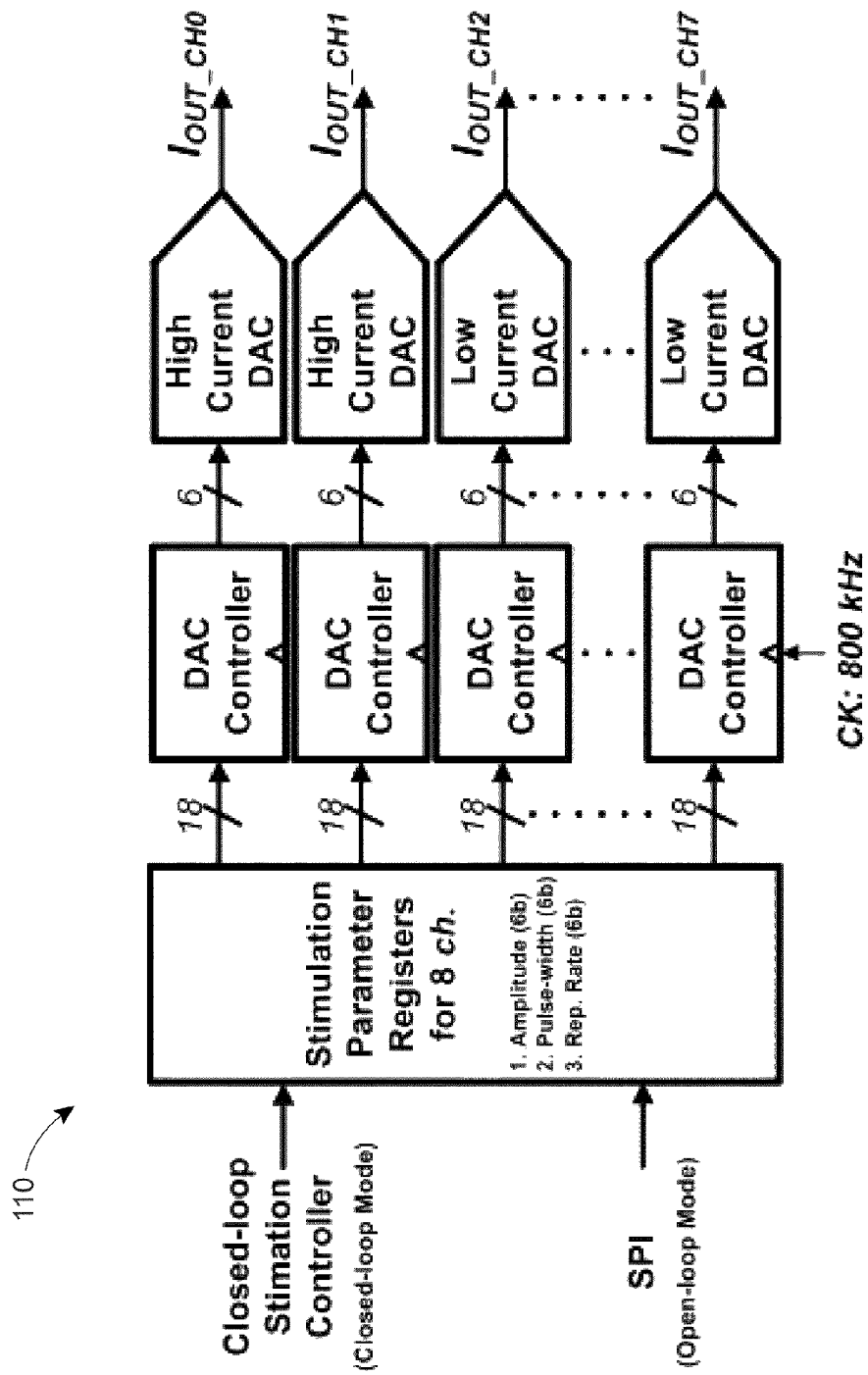
FIG. 12 is a schematic of one embodiment of an 8-channel current stimulator.

In one embodiment, the system and method may implement a programmable current stimulator 110 to deliver neurostimulation, as shown in FIG. 12. Biphasic stimulation may be chosen to avoid tissue damage caused by residual charge. Various stimulation parameters may be altered to optimize treatment, including amplitude, pulse width, and stimulating frequency of the stimulation current.

The current stimulator 110 may be made up of three parts: eight 6-bit current steering digital to analog converters (DACs) 122, dedicated DAC controllers for each current DAC 124, and stimulation parameter registers 126. DAC controllers 124 may control current DACs according to the stimulation parameter input from the registers to generate biphasic stimulation current. In order to support a variety of stimulation probes, six DACs may be used to drive current up to 116 μA, and two other DACs may be used to drive current up to 4.2 μA. Additionally, the high current channels may drive miniature LEDs for optogenetic applications as well as DBS probes. A triple cascode current-steering DAC may be utilized for its high linearity.

Figure 13:
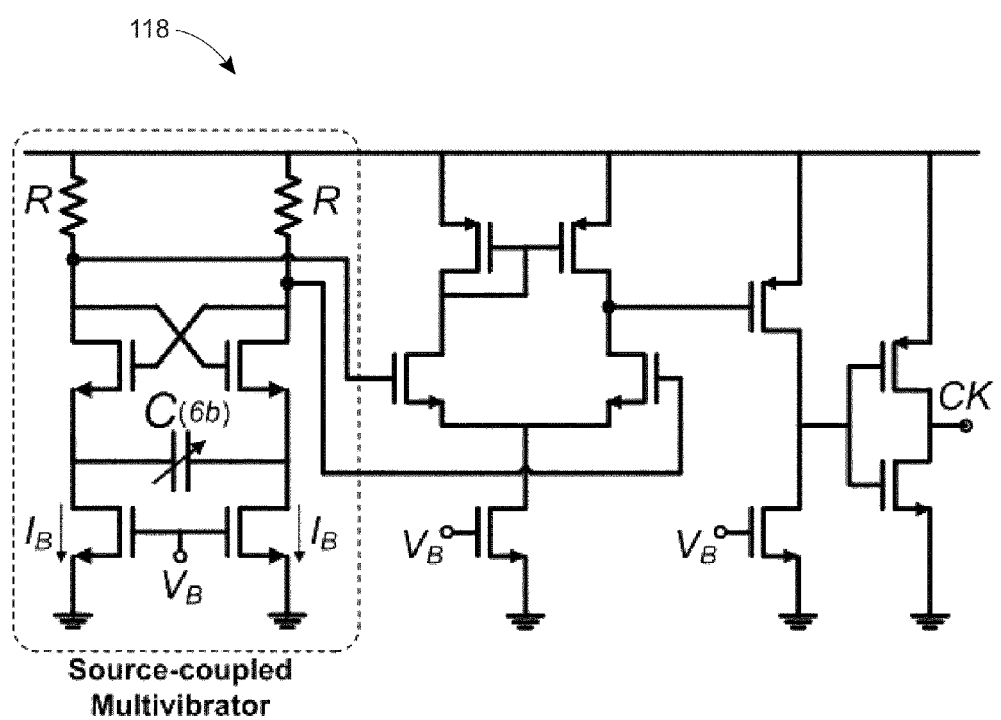
FIG. 13 is a schematic of one embodiment of a clock generator.

In one embodiment, the system and method may implement a clock generator 118, as shown in FIG. 13. A relaxation oscillator may be used, as it can save space by not requiring inductors. A source-coupled multivibrator, for example, is a relaxation oscillator that may be used to generate an 800 kHz on-chip clock signal for the entire system. As shown in FIG. 13, amplifiers and an inverter may be used to follow a source-coupled multivibrator to generate a rail-to-rail clock. A 6-bit digitally controlled capacitor array may be implemented in the design to provide an accurate 800 kHz output, even with significant process variation.

Figure 14:
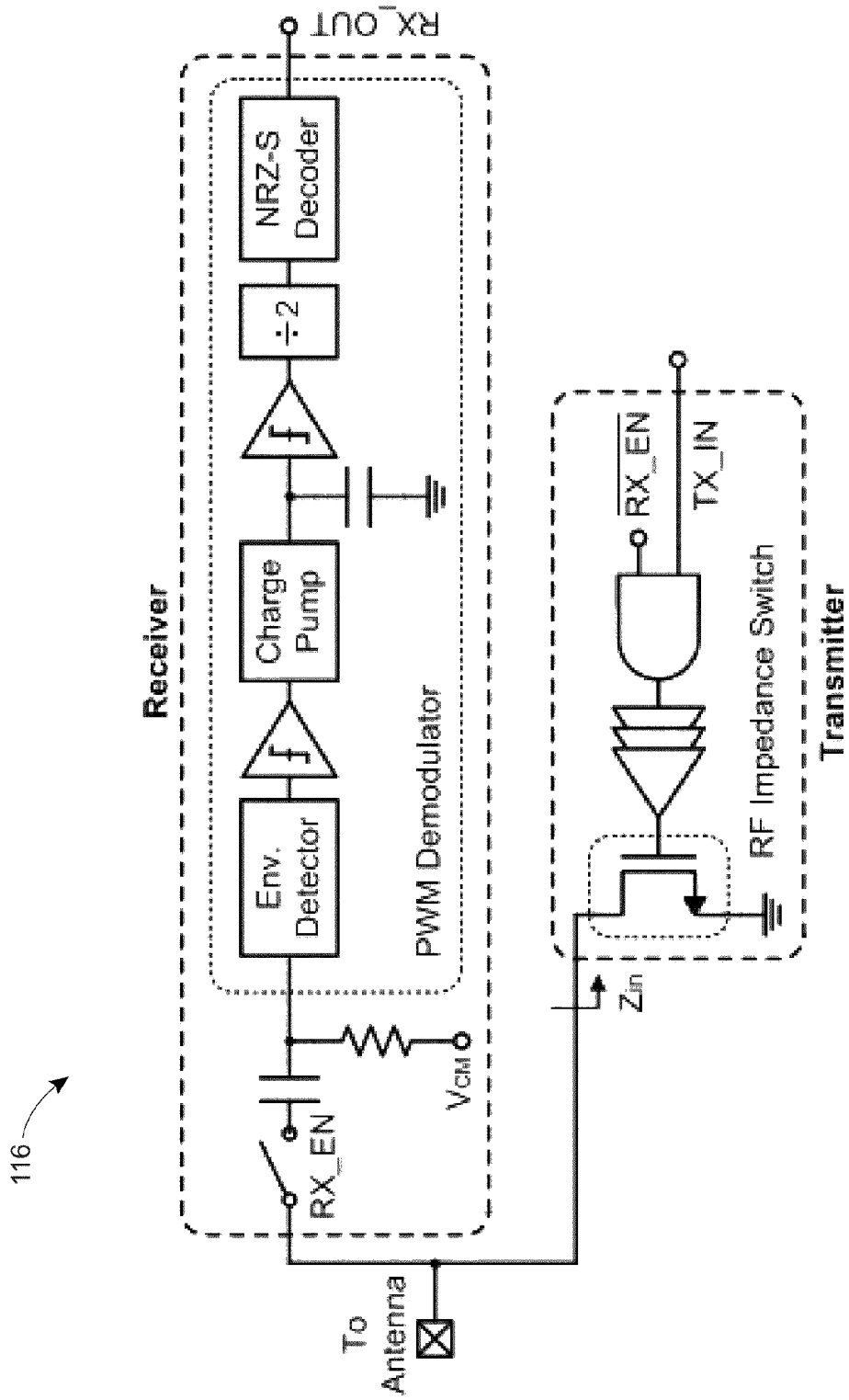
FIG. 14 is a block diagram of one embodiment of an RF transceiver.

In one embodiment, the system and method may implement a radio frequency transceiver 116, as shown in FIG. 14. This transceiver 116 may be used to monitor the states of a patient or the device itself. Specifically, a backscatter type communication scheme may be used for its extremely low power consumption and simplicity of design on the transponder side. An 800 kbps power-efficient backscatter RF transmitter may communicate recorded LFP, spike, or raw data wirelessly to an external receiver for further analysis. The RF transceiver 116 may also enable manual stimulation parameter-setting through wireless communication.

As shown in FIG. 14, the transceiver 116 may be a half-duplex type that works as a receiver or transmitter depending on a digital mode control bit, RX_EN. The transmitter may simply consist of buffers and a switch transistor for impedance modulation. The receiver may function based on a pulse-width modulation (PWM) scheme.

Figure 15:
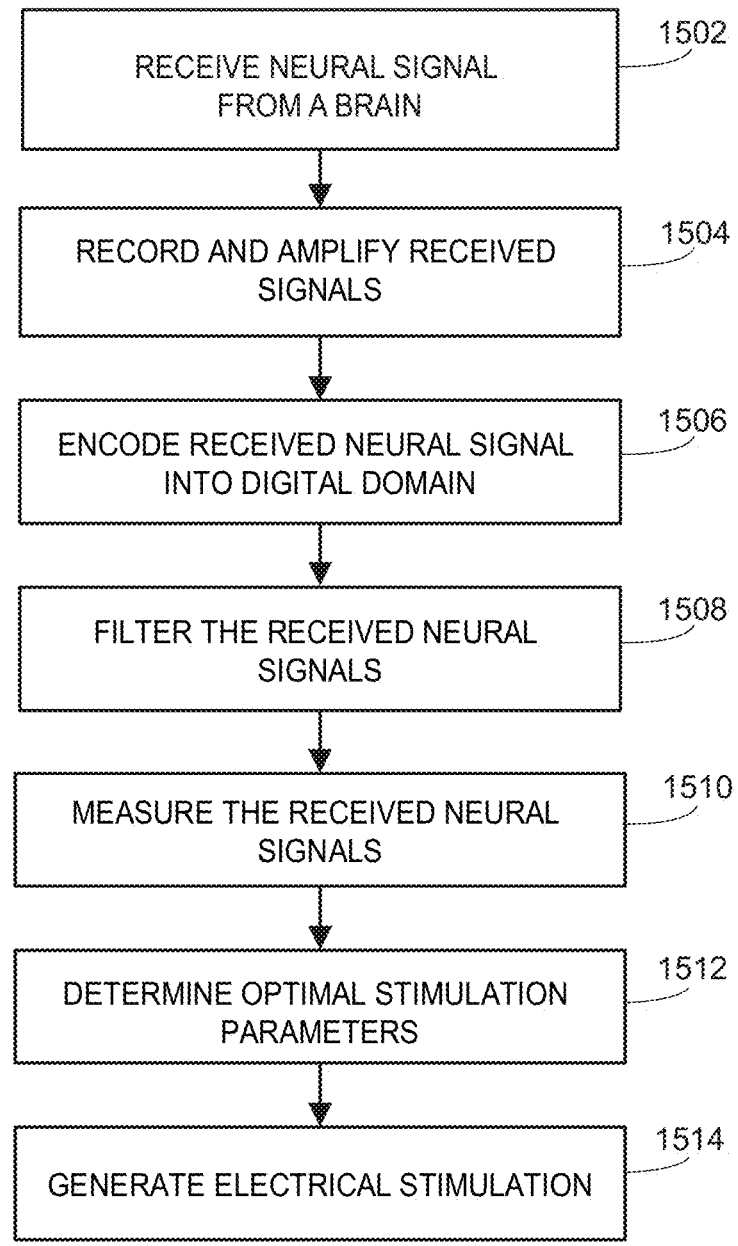
FIG. 15 is a block diagram of one embodiment of a DBS process.

FIG. 15 illustrates a block diagram of an exemplary method for conducting closed loop deep brain stimulation. The method may include receiving a neural signal from a brain (block 1502). In one embodiment the signals may be local field potential signals. The method may then record and amplify the received signals (block 1504). The method may further include encoding the amplified neural signals into the digital domain (block 1506) and filtering the encoded signals (block 1508). The method may then include measuring the encoded signals (block 1510) and determining optimal stimulation parameters (block 1512) which then may be used to generate electrical stimulation (block 1514). This method may be encoded on a computer-readable storage medium comprising computer-readable instructions stored thereon, executed on a processor of a system.

Figure 17A:
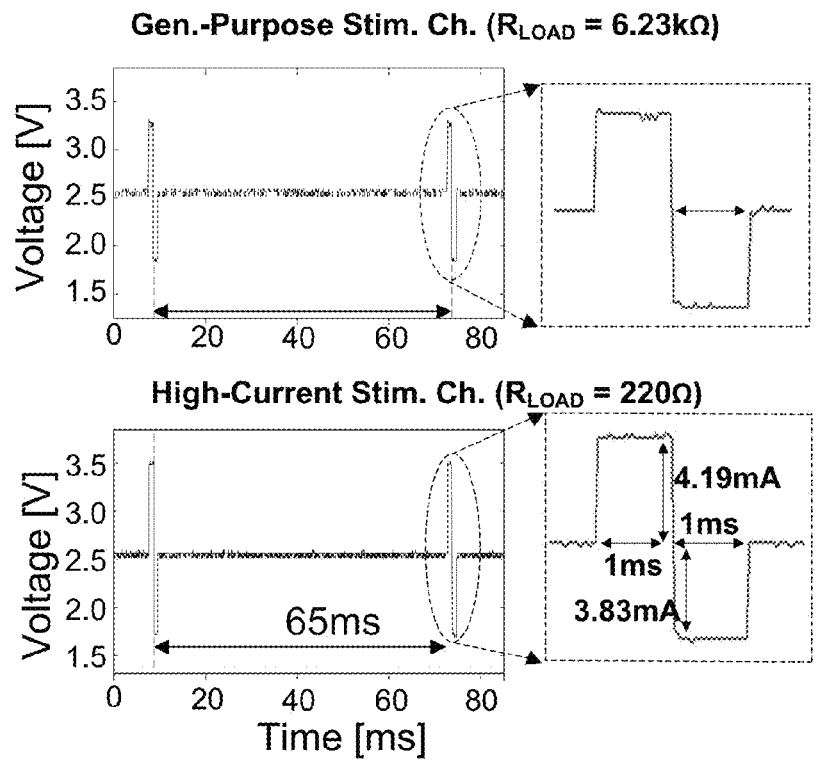
FIG. 17A is a schematic of a measured stimulation current waveforms of low-current and high-current stimulation channels with 6.23 kΩ and 220Ω respectively.
Figure 17B:
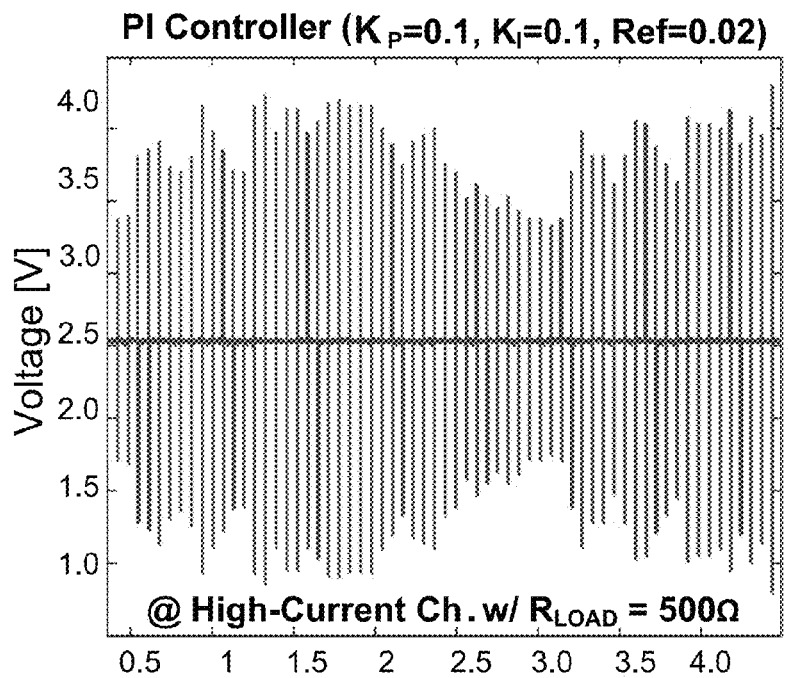
FIG. 17B is a schematic of a high-current stimulation channel in closed loop mode using LFP energy detection.
Figure 18:
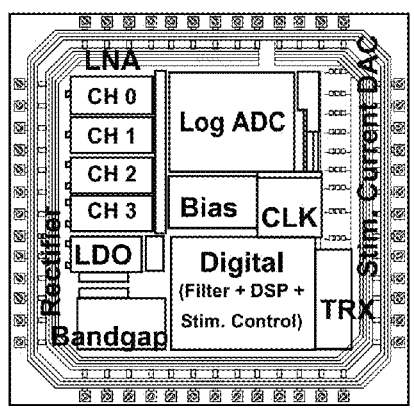
FIG. 18 is a schematic of a die micrograph of one embodiment of a log-based closed loop DBS system.

FIGS. 16-17 depict results of testing of a prototype system-on-chip (SoC) which is shown in FIG. 18. Specifically, FIG. 16A shows the measured output spectrum of the analog front-end. The SNDR of the analog front-end (4-ch. LNAs and log-ADV combined) is 35.5 dB at an input frequency of 170.898 Hz.

Figure 16A:
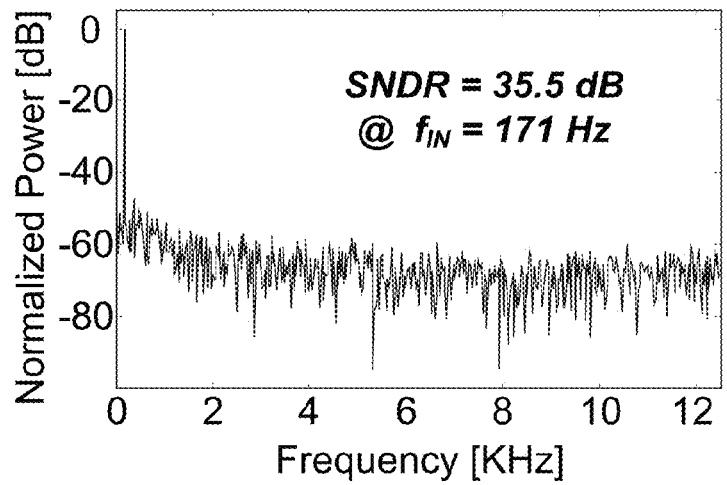
FIG. 16A is a schematic of a measured output spectrum of the designed analog front-end (4-ch. LNAs+log ADC).
Figure 16B:
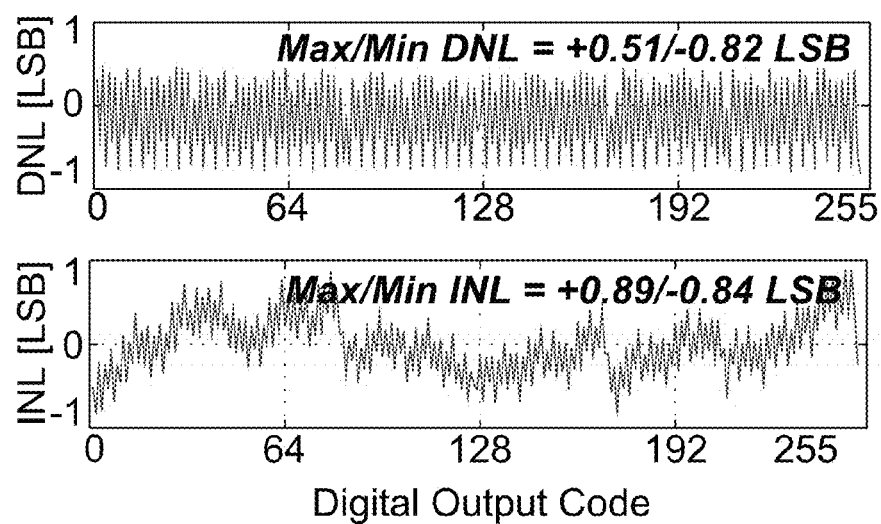
FIG. 16B is a schematic of a measured DNL and INL of the designed analog front-end (4-ch. LNAs+log ADC).

FIG. 16B shows the measured DNL/INL of the analog front-end. Signals of amplitude 1.2 mV are applied for the DNL/INL and output spectral measurement of analog front end. The maximum DNL/INL is 0.82 LSB/0.89 LSB.

Figure 16C:
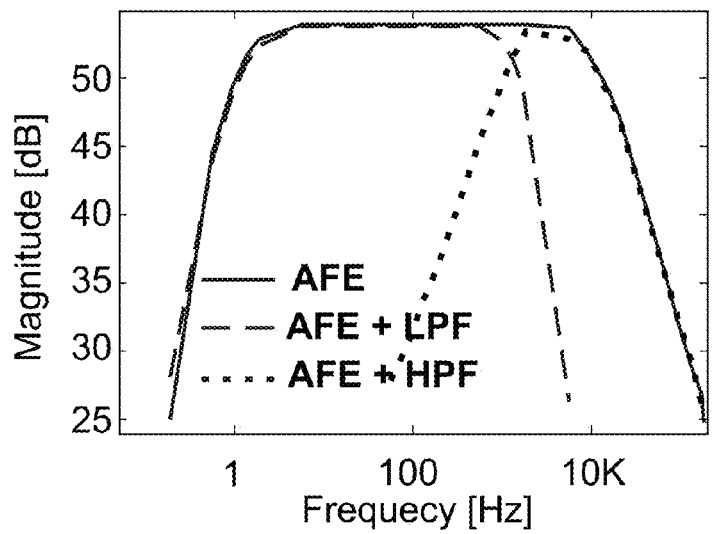
FIG. 16C is a schematic of a measured frequency response of the designed analog front-end (4-ch. LNAs+log ADC).

FIG. 16C shows the measured frequency response of the two sets of $15^{th}$ order digital FIR low-pass and high-pass filters implemented in the prototype to separate the low-frequency LFPs and the high frequency spikes from the digitized neural data of the two channels simultaneously. Both the LFP and HFP have the same 3 dB cutoff frequency of 700 Hz. In this prototype, the more energy efficient operation of addition can be used in place of multiplication due to the use of log domain processing, and the equivalence of addition in the log domain with multiplication in the linear domain. The prototype utilizes a lookup table for logarithmic accumulation. If the difference of the two inputs is larger than a threshold, the output of accumulation is approximated by the larger input, obviating the need for table lookup.

Figure 16D:
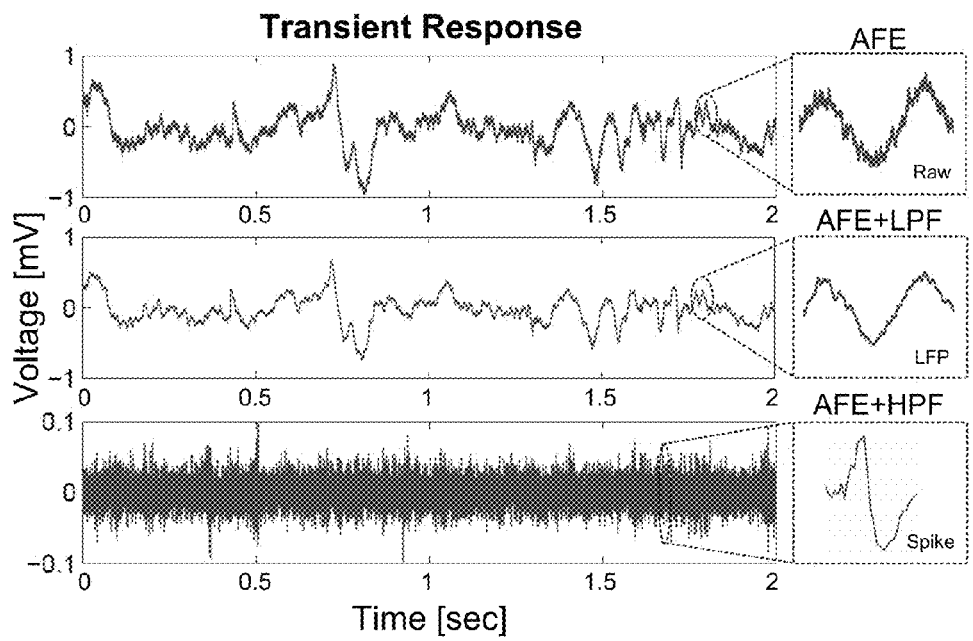
FIG. 16D is a schematic of a recorded output of the designed analog front-end (4-ch. LNAs+log ADC) with a pre-recorded neural signal from a rodent's brain applied as input to the system.

FIG. 16D shows measured LFP and spike recordings of a pre-recorded neural signal from a rodent's brain. The prototype cleanly extracts LFPs, spikes, and raw signals.

FIG. 17A shows the measurements of a stimulation current pulse train created by the prototype's current stimulator. Both current stimulation channels show a pulse-width of 1 ms and a repetition rate of 15.4 Hz. Amplitudes of a low-current channel and a high-current channel are 116 μA and 4.19 mA, respectively. FIG. 17B shows a high-current stimulation channel in closed loop mode using LFP energy detection, demonstrating the ability of the prototype to adapt the stimulation current in real-time by responding to the energy of the LFP signals.

Referring again to the prototype in FIG. 18, a die micrograph of an embodiment fabricated in 180 nm CMOS is shown. The total area (excluding only I/O pads) is 2×2 mm$^2$. The embodiment is powered from a 915 MHz carrier signal generating 1.8V. The LNAs in the embodiment are comprised of a cascade of two active band-pass filters and achieve a measured gain of 54 dB over a passband from 0.64 Hz to 6 KHz. The log-ADC improves on that by removing the dead zone where signals are compressed below the quantization range. The function $Y=0.9|V_{in}/V_{range}|+0.1$ is applied within the SHA to remove this dead zone without losing dynamic range.

Figure 20:
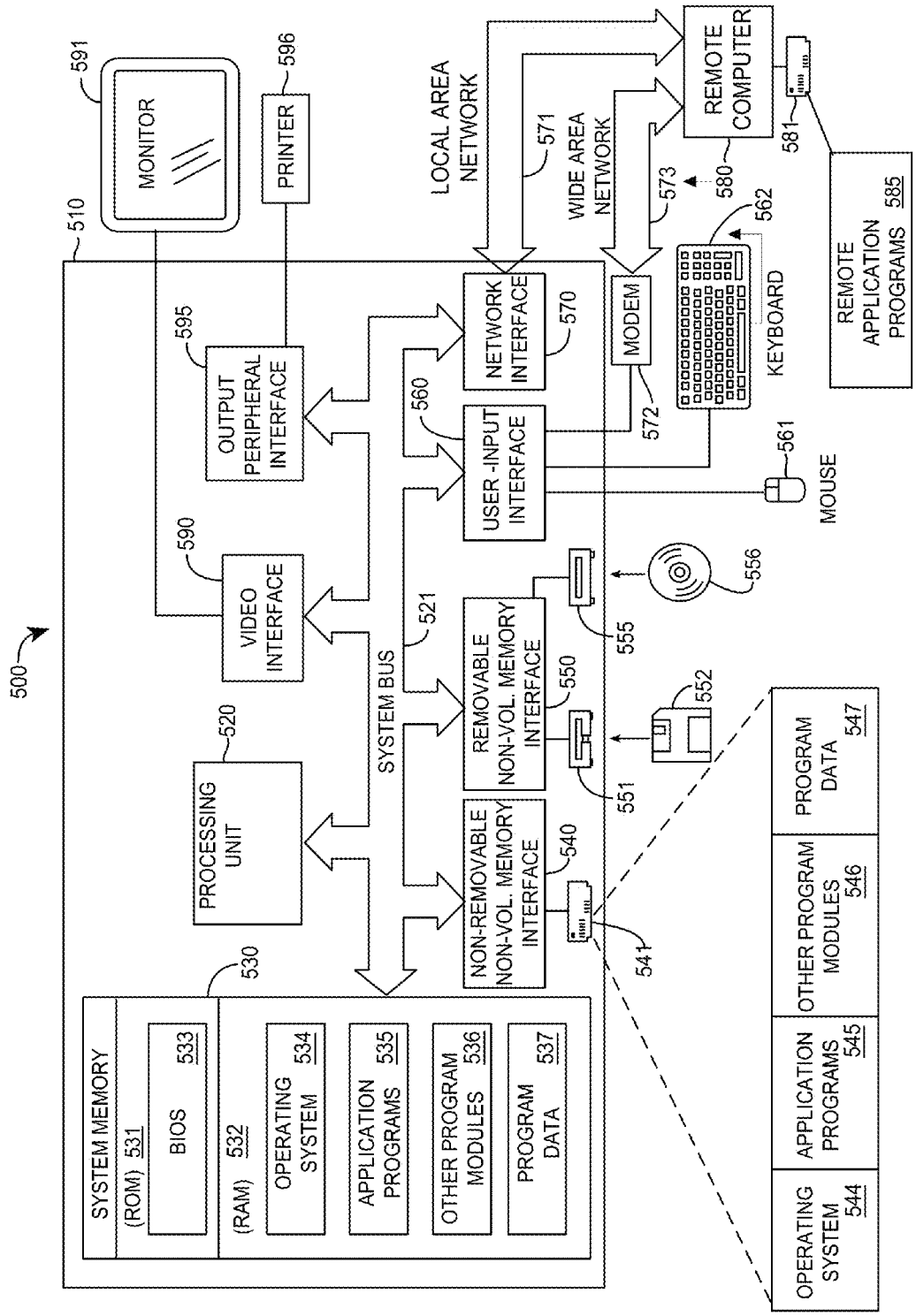
FIG. 20 is a block diagram showing an exemplary electronic device in the form of a computer supporting a closed-loop neural stimulation process.

With reference to FIG. 20, an exemplary system for implementing the claimed method and apparatus includes a general purpose computing device in the form of a computer 2110. Components shown in dashed outline are not technically part of the computer 2110, but are used to illustrate the exemplary embodiment of FIG. 20. Components of computer 2110 may include, but are not limited to, a processor 2120, a system memory 2130, a memory/graphics interface 2121 and an I/O interface 2122. The system memory 2130 and a graphics processor 2190 may be coupled to the memory/graphics interface 2121. A monitor 2191 or other graphic output device may be coupled to the graphics processor 2190.

A series of system busses may couple various system components including a high speed system bus 2123 between the processor 2120, the memory/graphics interface 2121 and the I/O interface 2122, a front-side bus 2124 between the memory/graphics interface 2121 and the system memory 2130, and an advanced graphics processing (AGP) bus 2125 between the memory/graphics interface 2121 and the graphics processor 2190. The system bus 2123 may be any of several types of bus structures including, by way of example, and not limitation, such architectures include Industry Standard Architecture (ISA) bus, Micro Channel Architecture (MCA) bus and Enhanced ISA (EISA) bus. As system architectures evolve, other bus architectures and chip sets may be used but often generally follow this pattern. For example, companies such as Intel and AMD support the Intel Hub Architecture (IHA) and the Hypertransport™ architecture, respectively.

The computer 2110 typically includes a variety of computer readable media. Computer readable media can be any available media that can be accessed by computer 2110 and includes both volatile and nonvolatile media, removable and non-removable media. By way of example, and not limitation, computer readable media may comprise computer storage media. Computer storage media includes both volatile and nonvolatile, removable and non-removable media implemented in any method or technology for storage of information such as computer executable instructions, data structures, program modules or other data. Computer storage media includes RAM, ROM, EEPROM, flash memory or other memory technology, CD-ROM, digital versatile disks (DVD) or other optical disk storage, magnetic cassettes, magnetic tape, magnetic disk storage or other magnetic storage devices, data stores, or other physical storage elements that physically embody electronic data and excludes any propagated media such as radio waves or modulated carrier signals.

The system memory 2130 includes computer storage media in the form of volatile and/or nonvolatile memory such as read only memory (ROM) 2131 and random access memory (RAM) 2132. The system ROM 2131 may contain permanent system data 2143, such as computer-specific data that may be used as a seed for generating random numbers or nonces, for example, for use in item selection and statistical calculations. RAM 2132 typically contains data and/or program modules that are immediately accessible to and/or presently being operated on by processor 2120. By way of example, and not limitation, FIG. 20 illustrates operating system 2134, application programs 2135, other program modules 2136, and program data 2137.

The I/O interface 2122 may couple the system bus 2123 with a number of other busses 2126, 2127 and 2128 that couple a variety of internal and external devices to the computer 2110. A serial peripheral interface (SPI) bus 2126 may connect to a basic input/output system (BIOS) memory 2133 containing the basic routines that help to transfer information between elements within computer 2110, such as during start-up.

A super input/output chip 2160 may be used to connect to a number of 'legacy' peripherals, such as floppy disk 2152, keyboard/mouse 2162, and printer 2196, as examples. The super I/O chip 2160 may be connected to the I/O interface 2122 with a bus 2127, such as a low pin count (LPC) bus, in some embodiments. Various embodiments of the super I/O chip 2160 are widely available in the commercial marketplace. In one embodiment, bus 2128 may be a Peripheral Component Interconnect (PCI) bus.

The computer 2110 may also include other removable/non-removable, volatile/nonvolatile computer storage media. By way of example only, FIG. 20 illustrates a hard disk drive 2140 that reads from or writes to non-removable, nonvolatile magnetic media. The hard disk drive 2140 may be a conventional hard disk drive.

Removable media, such as a universal serial bus (USB) memory 2153, firewire (IEEE 1394), or CD/DVD drive 2156 may be connected to the PCI bus 2128 directly or through an interface 2150. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like.

The drives and their associated computer storage media discussed above and illustrated in FIG. 20, provide storage of computer readable instructions, data structures, program modules and other data for the computer 2110. In FIG. 20, for example, hard disk drive 2140 is illustrated as storing operating system 2144, application programs 2145, other program modules 2146, and program data 2147. Note that these components can either be the same as or different from operating system 2134, application programs 2135, other program modules 2136, and program data 2137. Operating system 2144, application programs 2145, other program modules 2146, and program data 2147 are given different numbers here to illustrate that, at a minimum, they are different copies. A user may enter commands and information into the computer 2110 through input devices such as a mouse/keyboard 162 or other input device combination. Other input devices (not shown) may include a microphone, joystick, satellite dish, scanner, or the like. These and other input devices are often connected to the processor 2120 through one of the I/O interface busses, such as the SPI 2126, the LPC 2127, or the PCI 2128, but other busses may be used. In some embodiments, other devices may be coupled to parallel ports, infrared interfaces, game ports, and the like (not depicted), via the super I/O chip 2160.

The computer 2110 may operate in a networked environment using logical communication ports to one or more remote computers, such as a remote computer 2180 via a network interface controller (NIC) 2170. The remote computer 2180 may be a personal computer, a server, a router, a network PC, a peer device or other common network node, and typically includes many or all of the elements described above relative to the computer 2110. The logical connection between the NIC 2170 and the remote computer 2180 depicted in FIG. 20 may include a local area network (LAN), a wide area network (WAN), or both, but may also include other networks. Such networking environments are commonplace in offices, enterprise-wide computer networks, intranets, and the Internet.

The invention claimed is:

1. A method for conducting deep brain stimulation of an individual, the method comprising:
   receiving neural signals from a brain;
   recording the received neural signals into a memory;
   amplifying, via an amplifier module, the received neural signals;
   encoding, via a logarithmic analog-to-digital converter module, the amplified neural signals into a digital domain;
   filtering in the logarithmic domain, via a logarithmic digital filter module, the encoded neural signals;
   measuring the filtered neural signals;
   calculating at least one optimal stimulation parameter, via a digital signal processor, based on the measured neural signals;
   generating, via a stimulator module, a stimulation signal based on the calculated at least one optimal stimulation parameter; and
   transmitting the generated stimulation signal to the individual.

2. The method of claim 1, wherein the received neural signals include at least one local field potential (LFP) signal and/or at least one high frequency spike neural signal.

3. The method of claim 1, wherein the amplifier is a low-noise neural amplifier arranged in a two-stage cascade structure.

4. The method of claim 1, wherein the encoding into the digital domain via logarithmic analog-to-digital converter module includes pre-converting the received neural signals to remove a logarithmic dead zone.

5. The method of claim 1, wherein filtering the encoded neural signals via the logarithmic digital filter module involves separating low frequency LFP signals and high frequency neural spike signals.

6. The method of claim 1, wherein measuring the filtered neural signals includes utilizing bit-shifting to measure local field potential energy.

7. The method of claim 1, further comprising powering the digital signal processor with a radio frequency-DC converter.

8. The method of claim 1, further comprising generating a time signal via a clock generator module.

9. The method of claim 1, further comprising utilizing a radio frequency transceiver to monitor the individual's brain state.

10. An apparatus for conducting deep brain stimulation on an individual, the apparatus comprising:
    an amplifier module for receiving, recording, and amplifying neural signals received from the individual;

a logarithmic analog-to-digital converter (ADC) module operatively connected to the amplifier module, the logarithmic analog-to-digital converter module being capable of encoding neural signals received from the amplifier module into the digital domain;

a logarithmic digital filter module operatively connected to the logarithmic analog-to-digital converter module, the logarithmic analog-to-digital converter module being capable of filtering, in the logarithmic domain, encoded neural signals received from the logarithmic analog-to-digital converter module;

a digital signal processor (DSP) module operatively connected to the logarithmic analog-to-digital converter module and capable of measuring filtered neural signals received from the logarithmic digital filter module and of calculating at least one optimal stimulation parameter based on the measured neural signals received from the digital processor module;

a stimulator module operatively connected to the digital signal processor and capable of generating a stimulation signal based on at least one calculated optimal stimulation parameter; and a transmitter module for transmitting the generated stimulation signal to the individual.

11. The apparatus of claim 10, wherein the amplifier module is configured to receive signals comprised of local field potential (LFP) signals and high frequency spike neural signals.

12. The apparatus of claim 10, wherein the amplifier module is a low-noise neural amplifier arranged in a two-stage cascade configuration.

13. The apparatus of claim 10, wherein the logarithmic analog-to-digital converter is configured to pre-convert the received neural signal to remove the logarithmic dead zone.

14. The apparatus of claim 10, wherein the logarithmic digital filter module is configured to separate the low frequency LFP signals and high frequency neural spike signals.

15. The apparatus of claim 10, wherein the digital signal processor is configured to measure the local field potential signal energy using bit-shifting.

16. The apparatus of claim 10, further comprising a power management module including a radio frequency-DC converter module and capable of providing power to at least one of the amplifier module, logarithmic analog-to-digital converter module, logarithmic digital filter module, digital signal processor, and stimulator module.

17. The apparatus of claim 10, further comprising a clock generator module operatively connected to the analog-to-digital converter module.

18. The apparatus of claim 10, further comprising a radio frequency transceiver module operatively connected to the logarithmic digital filter module.

19. A non-transitory computer-readable storage medium comprising computer-readable instructions stored thereon and to be executed on a processor of a system for conducting deep brain stimulation on an individual, the stored instructions comprising:

receiving neural signals from the individual's brain;
recording the received neural signals into a memory;
amplifying, via an amplifier module, the received neural signals;
encoding, via a logarithmic analog-to-digital converter module, the amplified neural signals into a digital domain;
filtering in the logarithmic domain, via a logarithmic digital filter module, the encoded neural signals;
measuring the filtered neural signals;
calculating at least one optimal stimulation parameter, via a digital signal processor, based on the measured neural signals;
generating, via a stimulator module, a stimulation signal based on the calculated at least one optimal stimulation parameter; and
transmitting the generated stimulation signal to the individual.

* * * * *